US00PP27182P3

(12) United States Plant Patent
Hendon, Jr.

(10) Patent No.: US PP27,182 P3
(45) Date of Patent: Sep. 20, 2016

(54) ***LAVANDULA* PLANT NAMED 'BRIDGET CHLOE'**

(50) Latin Name: *Lavandula×intermedia*
Varietal Denomination: Bridget Chloe

(71) Applicant: John Thomas Hendon, Jr., Blairsville, GA (US)

(72) Inventor: John Thomas Hendon, Jr., Blairsville, GA (US)

( * ) Notice: Subject to any disclaimer, the term of this patent is extended or adjusted under 35 U.S.C. 154(b) by 53 days.

(21) Appl. No.: 14/121,105

(22) Filed: Aug. 1, 2014

(65) Prior Publication Data

US 2016/0037701 P1 Feb. 4, 2016

(51) Int. Cl.
*A01H 5/00* (2006.01)

(52) U.S. Cl.
USPC ..... Plt./445

(58) Field of Classification Search
USPC ..... Plt./445
See application file for complete search history.

*Primary Examiner* — Susan McCormick Ewoldt

(57) ABSTRACT

A new cultivar of Lavender plant named 'Bridget Chloe' that is characterized by vivid purple flower buds, a rounded overall shape with large mounding habit, green bracts throughout bloom, multi scented fragrance, and resistance to *Septoria* Leaf Spot and the Alfalfa Mosaic Virus.

5 Drawing Sheets

Latin name: *Lavandula×intermedia.*
Varietal denomination: 'Bridget Chloe'.

FIELD OF THE INVENTION

The invention represents a new and distinct cultivar, with the Botanical Classification of *Lavandula×intermedia*, named 'Bridget Chloe'. The plant's new and distinguishable characteristics would be offered to the nursery industry in the form of a new Lavender cultivar with high visual and complex fragrance attributes, and having a quality of high survival success in a temperate environment where sultry summer heat, moderately cold winters, and high humidity conditions exist.

DESCRIPTION OF THE RELATED ART

In the late summer of 2002, new Lavender plants created from cuttings taken from two *Lavandula×intermedia* 'Provence' plant cultivars were planted southeast of Blairsville, Ga. These asexual reproductions were planted in a prepared cultivated contour row, having an elevation of 2,130 feet above sea level. In the early summer of the following year, 2003, subsequent cuttings were taken from the previous year's asexual reproductions of the initial two Lavender 'Provence' plant cultivars and placed into this cultivated row. In June of 2010, it was observed that some of the Lavender plants in this older row of Lavender showed deeper purple in their flower heads than the remainder of the Lavender 'Provence' plants that had been planted out in this row and had been harvested in previous years without any noticed change. Upon further examination of these new plants, it was observed that they had a pleasing and different fragrance from that of the Lavender 'Provence' plant cultivars that were originally planted in the cultivated row. It is unsure of how these plants, offering new morphological expressions, changed. The claimed new Lavender plant cultivar likely resulted from natural and/or environmental conditions in their growing environment, resulting in whole plant mutations.

Under careful observation, all subsequent clones taken from the discovered new Lavender plant cultivar have been uniform, stable, and reproduced true to type in successive generations of asexual reproduction.

SUMMARY OF THE INVENTION

Lavender 'Bridget Chloe' exhibits: Deep purple to vivid purple flowers

Lavender 'Bridget Chloe' exhibits: Deep green to silver-green/gray foliage color Lavender 'Bridget Chloe' exhibits: Resistance to *Septoria* Leaf Spot and the Alfalfa Mosaic Virus Lavender 'Bridget Chloe' exhibits: An impressive ornamental with a rounded overall shape, suitable for border and group plantings and row crops Lavender 'Bridget Chloe' exhibits: Culinary use, and is both rabbit and deer resistant Lavender 'Bridget Chloe' exhibits: Large mounding habit with long conical flower spikes atop long stems, with fragrant notes containing a rich floral aroma While this new lavender cultivar shares some attributes with other Lavender cultivars, such as the Lavender cultivar 'Dutch' (not patented); Lavender cultivar 'Abrialii' (not patented); and Lavender 'Provence' (not patented), the plant from which the subject new plant cultivar was initially propagated; the overall characteristics of this new Lavender plant are notably different from the aforementioned Lavender cultivars. Also, it should not be confused with Lavender 'Gros Bleu' (not patented), a relatively new Lavender cultivar from France, with near navy blue flower heads, instead of deep purple to vivid purple found in Lavender 'Bridget Chloe'. Nor should it be confused with the Lavender plant cultivar, 'Phenomenal' (U.S. Plant Pat. No. 24,193), introduced in 2012 which has similar attributes, but with bluer bud color and light green to silver-gray leaves. The flower spikes in this new Lavender plant cultivar are not quite as narrow as Lavender 'Dutch', and they are a deep purple to vivid purple with dark purple calyxes in early flower development, unlike either Lavender 'Dutch' or Lavender 'Provence' which have violet-green calyxes. Also, the leaves are not as silvery-green and broad as Lavender 'Dutch'.

This new cultivar has proven to be hardy and disease free throughout the test period, whereas Lavender 'Abrialii', a close look alike, is subject to disease, has short plant life, has not been planted or introduced in any way to the property where Lavender 'Bridget Chloe' has been discovered (southeast of Blairsville, Ga.); and has purple to gray-blue calyxes instead of the green turning to dark purple calyxes of the new 'Bridget Chloe' cultivar. In addition, the subject Lavender's dried flower buds tend to be more elongated and just a bit thinner, are more richly floral in fragrance, and are not as easily separated from the flower spikes as is Lavender 'Provence'. The dried flower buds from Lavender 'Provence' for the most part are plump, very fragrant with a camphorous overtone, easily separate from the flower spikes, and turn gray as in the case for the majority of the *Lavandula×intermedia* cultivars. On the other hand, when harvested at peak calyx development, this new plant cultivar's dried flower buds partially hold their dark purple color.

BOTANICAL DESCRIPTION OF THE PLANT

Figure 1:
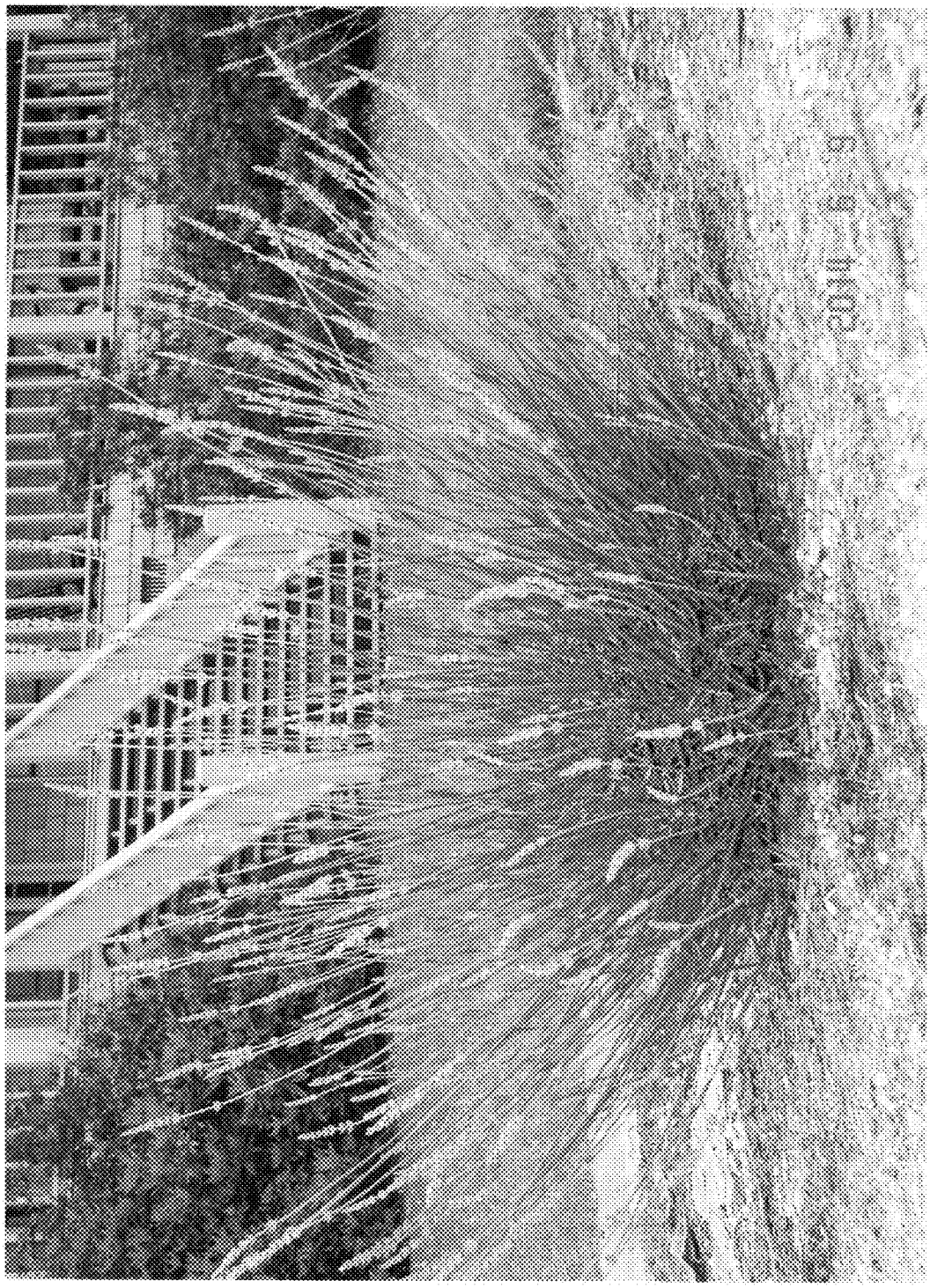
FIG. 1: Horizontal View showing Growth Habit of Plant in Early Flower Development. Depicts second year growth habit of the new plant cultivar in the early month of June, when the flower spikes are still developing. Note: uniform, compact habit of overall plant, and deep green foliage.
Figure 2:
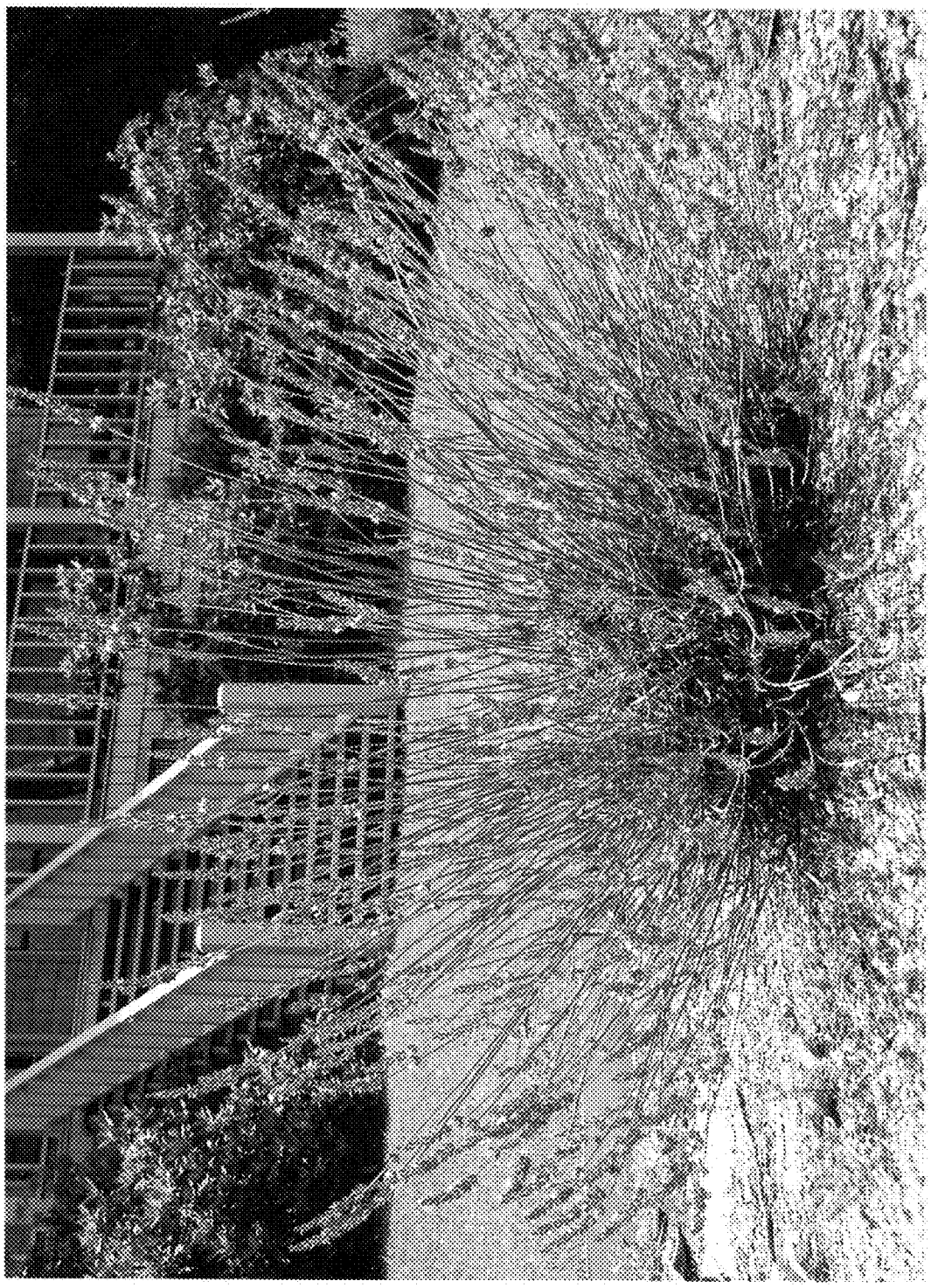
FIG. 2: Horizontal View showing Growth Habit of Plant at Mature Flower Development. Depicts second year growth habit of the new plant in mid to late June, when flower spikes are fully developed. Note: plant's mature flower heads; the spraying outwards, erect/semi-aslope growth form; and continued uniform, compact habit of the plant.
Figure 3:
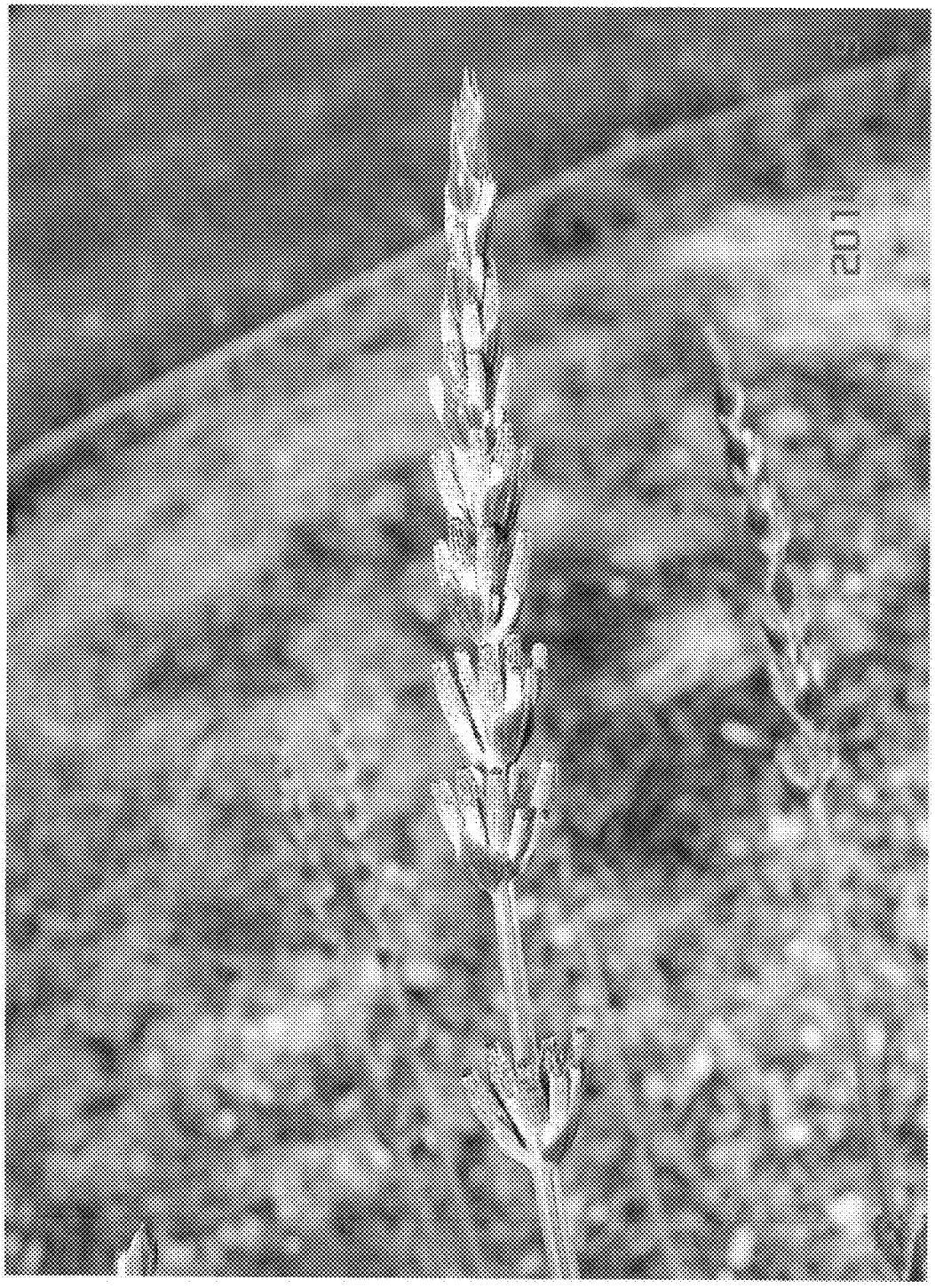
FIG. 3: Vertical View showing Close-up of Individual Flower Head in Early Plant Development. Depicts the individual parts of the plant's flowers in early plant development of the second year. Note: deep green flower bracts; and green turning to dark purple calyxes.
Figure 4:
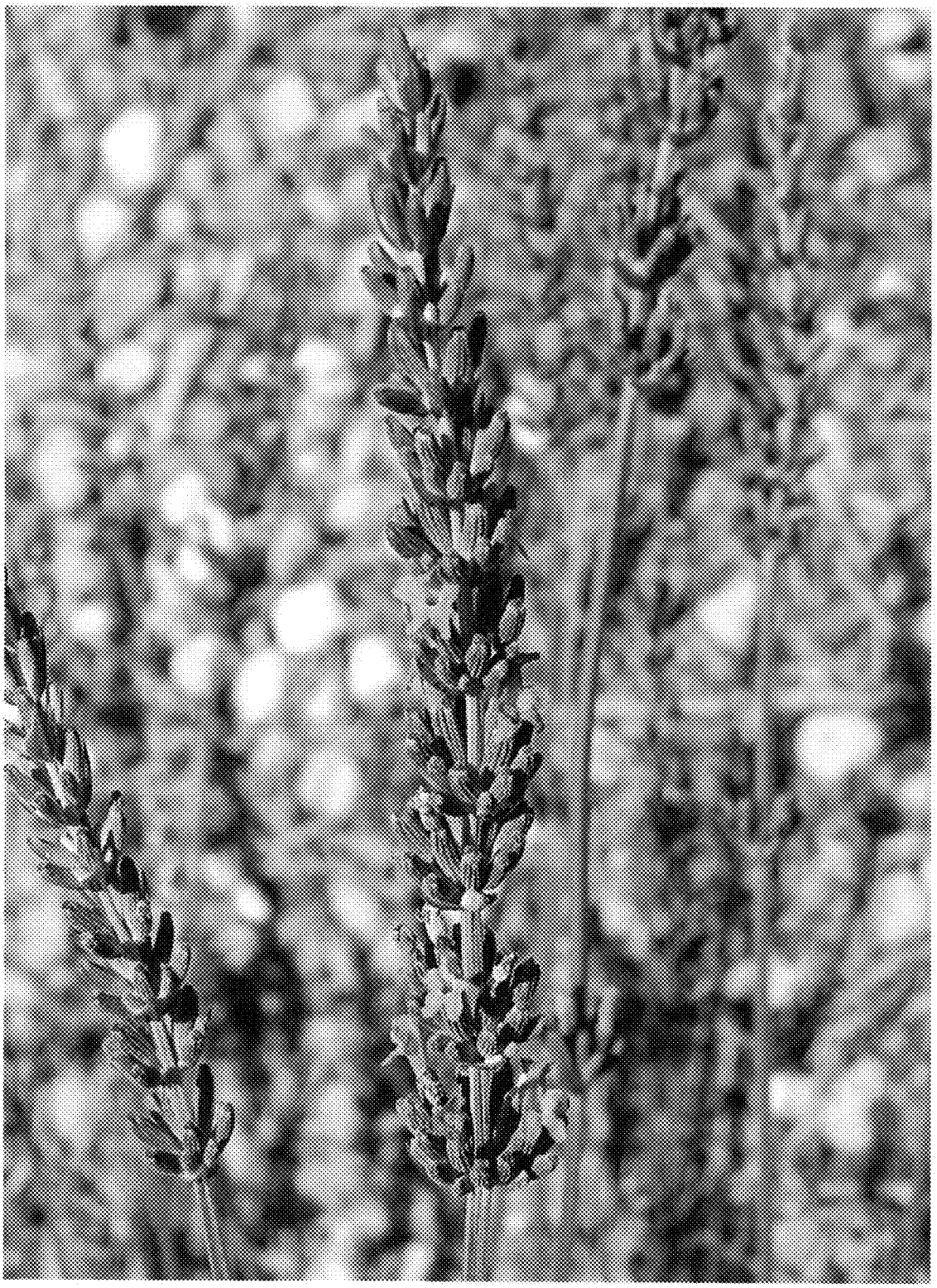
FIG. 4: Vertical View showing Close-up of Individual Flower Head at Flower Maturity. Depicts the individual parts of the plant's flowers at flower maturity in the second year. Note: dark purple calyxes; and deep purple to vivid purple corollas.
Figure 5:
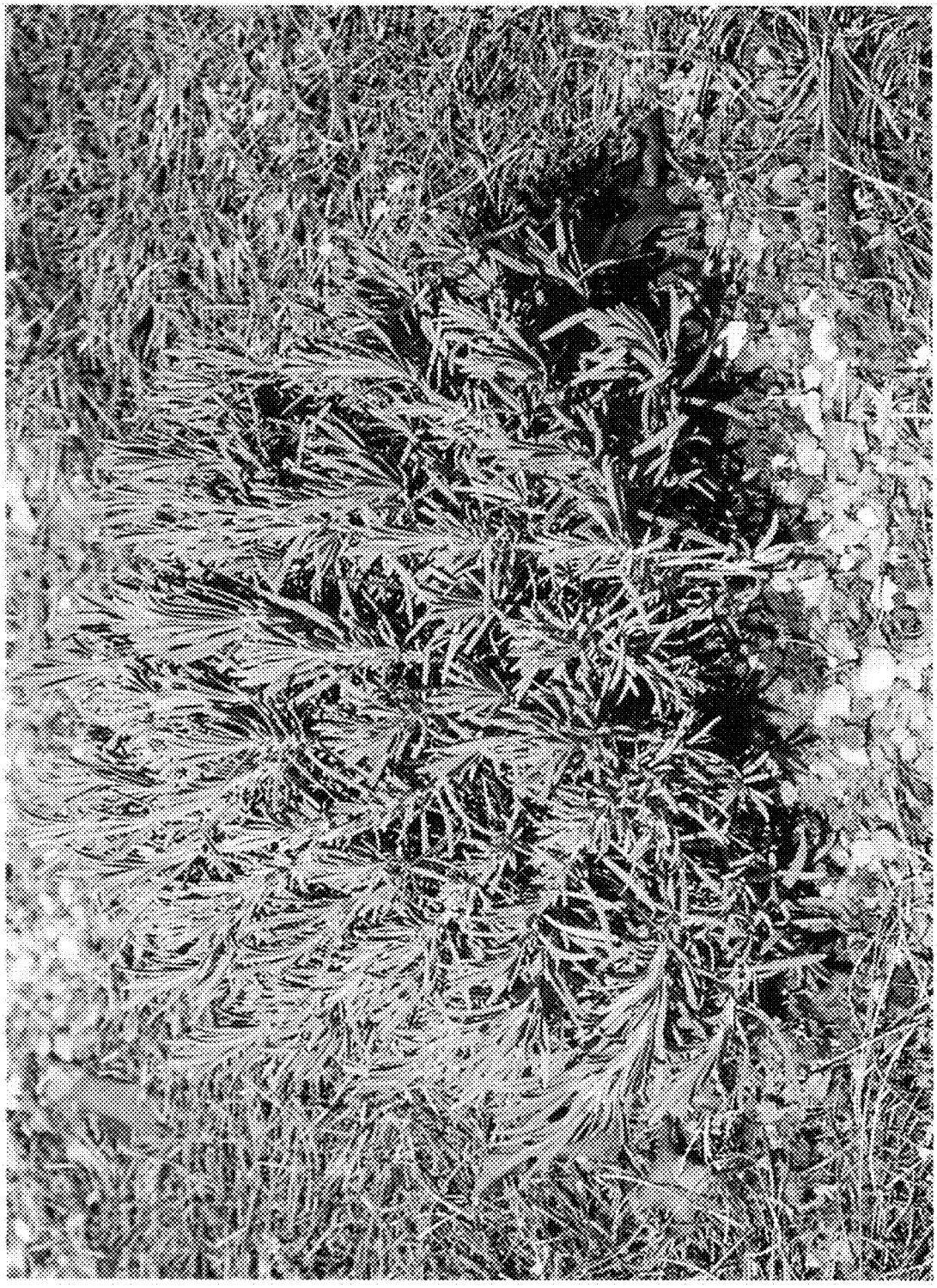
FIG. 5: Horizontal View showing Plant Habit in its Dormancy. Depicts plant's habit in its dormancy in the first year. Note: bluish, silver-green to grayish color of the foliage; and the compact habit.

The following is a detailed description of the new Lavender plant cultivar named 'Bridget Chloe'. Data was collected from an open cultivated row of the two year old plants located southeast of the City of Blairsville in Union County, Ga. The time of year was late spring to summer, and the average temperature was 26.2 to 27.5 degrees Centigrade in the day and 14.2 to 16.3 degrees Centigrade at night. The plants received eight to nine hours of sunlight on an average sunny day. Color determinations are in accordance with NBS-ISCC color dictionary, *Centroids by Number,* 1950s edition except where general color observations and terms of ordinary dictionary significance are used. The growing requirements are similar to the species. 'Bridget Chloe' has not been tested under all possible conditions and phenotypic differences may be observed with variations in environmental, climatic, and cultural conditions, however, without any variance in genotype.

Botanical classification: *Lavandula×intermedia.*

Annual or perennial: Perennial.

Parentage: 'Bridget Chloe' is a whole plant mutation of *Lavandula×intermedia* 'Provence'.

Vigor: Strong.

Growth habit: Upright, outwardly spreading.

Plant shape: Rounding, mounding, erect/Semi-Aslope growth form.

Height: Average from 61.6 to 76.8 centimeters (cm) for two year old plant.

Width: Average from 76.8 to 107.8 cm for two year old plant.

Hardiness: −14 to 38+ Celsius.

Propagation: Terminal tip cuttings.

Time to initiate roots: 14 to 16 days in summer.

Time to produce a rooted cutting: 21 days in summer.

Type of root system: Fine and fibrous.

Crop time: 9 months.

Stem:

- *Basal branching habit.*—Yes.
- *Number of lateral branches.*—Approximately 340.
- *Lateral branch diameter.*—2.5 mm. in diameter.
- *Lateral branch length.*—23 cm.
- *Lateral branch strength.*—Strong.
- *Color.*—NBS-ISCC No. 58, Moderate Brown.
- *Pubescence.*—Present, short fine hairs.
- *Internode length.*—1.3 cm. between nodes.
- *Shape.*—Square, becoming round at base.

Foliage:

- *Leaf arrangement.*—Opposite, two per node with approx. twelve axle stipules.
- *Compound or single.*—Single.
- *Quantity of leaves per lateral branch.*—34, with approx. 204 axle stipules.
- *Leaf shape.*—Linear.
- *Leaf apex.*—Acute.
- *Leaf attachment.*—Sessile, no petiole.
- *Leaf length.*—5.3 cm. in length.
- *Leaf width.*—4.0 mm. at center of leaf.
- *Texture.*—Velvety.
- *Pubescence.*—Present.
- *Leaf margin.*—Pinnate.
- *Young leaf color* (*upper surface*).—NBS-ISCC No. 118, Deep Yellow Green.
- *Young leaf color* (*lower surface*).—NBS-ISCC No. 119, Light Yellow Green.
- *Mature leaf color* (*upper surface*).—NBS-ISCC No. 118, Deep Yellow Green.
- *Mature leaf color* (*lower surface*).—NBS-ISCC No. 117, Strong Yellow Green.
- *Vein color* (*both surfaces*).—NBS-ISCC No. 119, Light Yellow Green.
- *Durability of foliage to stress.*—Strong.

Flower:

- *Flower arrangement.*—Terminal cylindrical spikes.
- *Inflorescence dimensions.*—6.1 cm. in length and 1.2 cm. in diameter.
- *Quantity of flowers and buds per inflorescence.*—Approximately 120.
- *Quantity of inflorescences per plant.*—Approximately 270.
- *Flowering season.*—Late Spring to early Summer.

*Time to flower or response time*.—2 weeks after buds form.

*Fragrance*.—Spicy-sweet, fresh, and aromatic floral notes.

*Taste*.—Aromatic, strong floral followed by a bitter end note.

*Self-cleaning or persistent*.—Self cleaning.

*Flower bud length*.—4 mm. in length.

*Flower bud diameter*.—5 mm. in diameter.

*Flower bud shape*.—Ovate.

*Bud color*.—NBS-ISCC No. 216, Vivid Purple.

*Flower aspect*.—Outward.

*Flower shape*.—Labiate.

*Flower dimensions*.—5 mm. in diameter and 7 mm. in height.

*Flower longevity*.—Lasts approximately 5 days.

*Petal arrangement*.—Rotate with five petals fused into a tube.

*Petal shape*.—Ligulate.

*Petal margin*.—Entire.

*Petal apex*.—Obtuse.

*Petal base*.—Fused.

*Petal texture*.—Smooth.

*Petal dimensions*.—4.0 mm. in length and 3.5 mm. in width.

*Petal color when opening* (*upper side*).—NBS-ISCC No. 216, Vivid Purple.

*Petal color when opening* (*under side*).—NBS-ISCC No. 216, Vivid Purple.

*Petal color at tube opening*.—NBS-ISCC No. 202, Very Pale Purplish Blue.

*Petal color fading to*.—No fading observed.

Sepals:

*Sepal number*.—2.

*Sepal shape*.—Ovate.

*Sepal apex*.—Obtuse.

*Sepal base*.—Fused Sepal margin, Entire.

*Sepal texture* (*both surfaces*).—Velvety/fine hairs.

*Sepal dimensions*.—6.0 mm. in length and 1.5 mm. in width.

*Sepal color* (*both surfaces*).—NBS-ISCC No. 119, Light Yellow Green to NBS-ISCC No. 220, Very Deep Purple.

Calyx:

*Calyx shape*.—Campanulate tube.

*Calyx dimensions*.—6.0 mm. in length and 1.5 mm. in diameter.

Peduncle:

*Peduncle dimensions*.—38 cm. in length and 2.5 mm. in diameter.

*Peduncle angle*.—0 to 30 degrees from vertical.

*Peduncle color*.—NBS-ISCC No. 119, Light Yellow Green.

*Peduncle strength*.—Strong.

Reproductive organs:

*Stamen number*.—4.

*Anther length*.—Not measured.

*Amount of pollen*.—Moderate.

*Pistil number*.—1.

*Pistil length*.—2.5 mm.

*Stigma shape*.—Club shaped.

*Style length*.—Not measured.

*Ovary color*.—Not observed.

Fruit and seed production: Fruit type is dry and does not split open when ripe. Plants of the new Lavender have not been observed for seed production.

Disease and pest resistance: The new Lavender is resistant to *Septoria* Leaf Spot and the Alfalfa Mosaic Virus, and is both rabbit and deer resistant.

Comprehensive color determinations of the reproductive organs have not been performed for the new Lavender.

It is claimed:

1. A new and distinct Lavender plant named 'Bridget Chloe' as herein described and illustrated.

* * * * *